United States Patent [19]

Reinhardt et al.

[11] Patent Number: 5,594,075
[45] Date of Patent: Jan. 14, 1997

[54] ACETYLENIC HETEROCYCLIC NONLINEAR OPTICAL THERMOSET MONOMERS

[75] Inventors: Bruce A. Reinhardt, Tipp City; Jayprakash C. Bhatt, Riverside, both of Ohio

[73] Assignee: The United States of America as represented by the Secretary of the Air Force, Washington, D.C.

[21] Appl. No.: 505,715

[22] Filed: Aug. 7, 1995

[51] Int. Cl.$^6$ .......................... C08G 73/22; C08G 75/32; C08L 79/06
[52] U.S. Cl. .......................... 525/426; 525/420; 525/434; 525/909
[58] Field of Search .................................. 525/426, 420, 525/434, 909

[56] References Cited

U.S. PATENT DOCUMENTS

| | | | |
|---|---|---|---|
| 4,108,835 | 8/1978 | Arnold et al. | 528/183 |
| 4,508,560 | 4/1985 | Brunner et al. | 71/94 |
| 4,626,272 | 12/1986 | Brunner et al. | 71/92 |
| 4,772,678 | 9/1988 | Sybert et al. | 528/179 |
| 5,066,541 | 11/1991 | Lubowitz et al. | 428/378 |
| 5,149,755 | 9/1992 | Perry | 528/210 |
| 5,151,489 | 9/1992 | Harris et al. | 528/183 |
| 5,216,117 | 6/1993 | Sheppard et al. | 528/322 |

OTHER PUBLICATIONS

J. Chem. Soc., Perkin Trans. 2 (1994), 8, 1771–5 Novak et al.
Synthesis (1984), 7, 571–2 Carpita et al.

*Primary Examiner*—Helen Lee
*Attorney, Agent, or Firm*—Charles E. Bricker; Thomas L. Kundert

[57] ABSTRACT

The compound 2-ethynyl-5-(4-pyridyl)ethynyl thiophene:

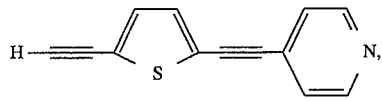

when incorporated into a thermoplastic polymer having repeating units of the formula:

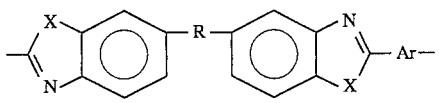

wherein X is —O— or —S—, and R is selected from the group consisting of:

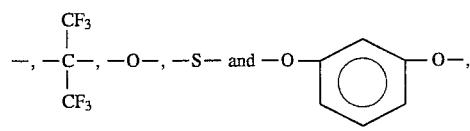

and Ar is selected from the group consisting of:

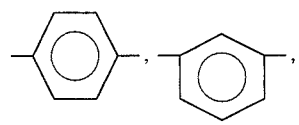

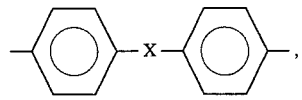

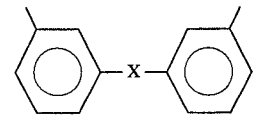

and

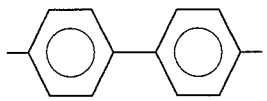

wherein X is as previously defined, poled to align the molecules and cured to crosslink at least the terminal acetylenic groups, has second-order nonlinear optical activity.

5 Claims, No Drawings

ACETYLENIC HETEROCYCLIC NONLINEAR OPTICAL THERMOSET MONOMERS

RIGHTS OF THE GOVERNMENT

The invention described herein may be manufactured and used by or for the Government of the United States for all governmental purposes without the payment of any royalty.

BACKGROUND OF THE INVENTION

The present invention relates to acetylenic monomers which can be cured to produce materials with nonlinear optical activity.

Considerable research effort has been directed toward the use of organic second-order nonlinear (NLO) polymers in practical devices. The predicted advantages of such organic polymers for frequency conversion and integrated optics applications is headed by potential ease of fabrication and low cost. The polymer properties necessary to efficiently frequency double light at 800 nm in a slab waveguide device include a $\chi^{(2)}$ of 60 pm/V ($\mu\beta=350\times10^{-30}$ esu D) and no absorption at 400 nm.

For a polymeric material to have successful application in an electro-optic (EO) device, it needs to possess a somewhat different set of properties. A practical EO polymer must be spin coatable, easily poled by an electric field or self-assembled, have optical losses below 1 dB/cm and be capable of producing devices with modulation bandwidths of 100 GHz. For a NLO EO polymer material to be commercially realistic, it must also be able to retain a reasonable second-order activity (>30 pm/V at 830 nm) at temperatures experienced during routine microelectronics circuit fabrication (as high as 320° C. for 20 min.). For military applications, it is further necessary that a material retain at least 95% of its original EO coefficient after 10 years at 125° C. Finally, the synthesis of any polymeric material for potential commercial use must address the issues of low cost producibility, toxicity/carcinogenicity and waste disposal.

We have prepared an acetylenic thermoset monomer which, when mixed with high performance thermoplastic materials, can be poled and cured at elevated temperatures to provide composites with second-order nonlinear optical (NLO) activity, improved thermal stability and optical transparency at wavelengths shorter than 830 nm.

Accordingly, it is an object of the present invention to provide an acetylenic thermoset monomer which, when mixed with high performance thermoplastic materials, can be poled and cured at elevated temperatures to provide composites with second-order nonlinear optical activity.

It is another object of the present invention to provide composite materials with second-order nonlinear optical activity.

Other objects and advantages of the present invention will be apparent to those skilled in the art.

SUMMARY OF THE INVENTION

In accordance with the present invention there is provided the compound 2-ethynyl-5-(4-pyridyl)ethynyl thiophene.

Also in accordance with the present invention there are provided poled and cured composite films with second-order nonlinear optical activity consisting essentially of about 5 to 30 weight percent 2-ethynyl-5-(4-pyridyl)ethynyl thiophene, balance a high performance thermoplastic polymer.

DETAILED DESCRIPTION OF THE INVENTION

The 2-ethynyl-5-(4-pyridyl)ethynyl thiophene is synthesized by the reaction sequence shown below. In the first step, bromination of 1-(2-thienyl)-2-(4-pyridyl)ethene followed by base-catalyzed dehydrohalogenation gives 2-bromo-5-{2-(4-pyridyl)ethynyl}thiophene (I):

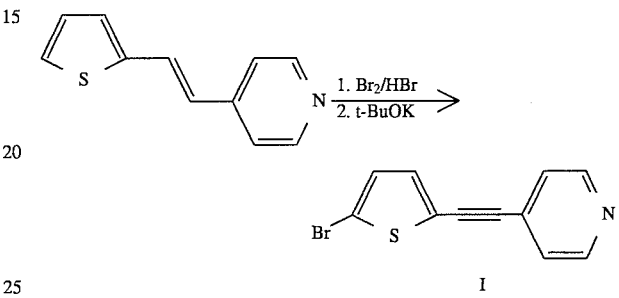

In the second step, the palladium catalyzed addition of 2-methyl-3-butyn-2-ol to compound I gives 2-{3-methyl-3-hydroxybutynyl}-5-{2-(4-pyridyl)ethynyl}thiophene (II):

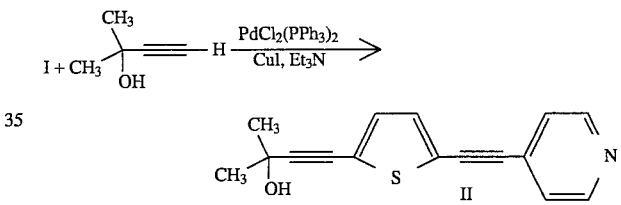

The term "Ph" in the palladium catalyst formula means "phenyl". In the third step, removal of the protecting group using KOH in methanol gives the acetylene-terminated thermoset monomer 2-ethynyl-5-(4-pyridyl)ethynyl thiophene (III):

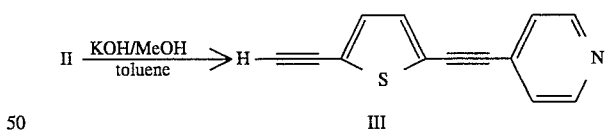

The thermoplastic polymer can be any thermoplastic polymer having a $T_g$ equal to or greater than the curing temperature of the 2-ethynyl-5-(4-pyridyl)ethynyl thiophene (about 145° C.) and which can be dissolved in a common solvent without being degraded. Illustrative examples of suitable thermoplastics include those consisting essentially of repeating units having the following formula:

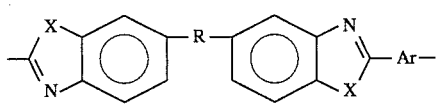

wherein X is —O— or —S—, and R is selected from the group consisting of:

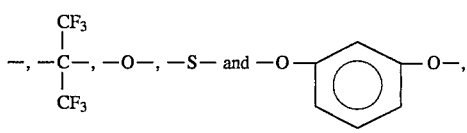

In the examples which follow, the thermoplastic polymer is referred to by the term 6F-PBO-1. This polymer has repeating units of the formula

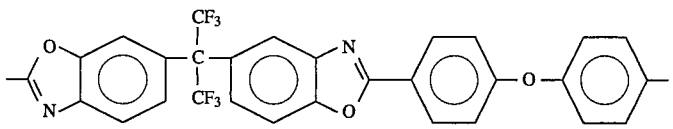

and Ar is selected from the group consisting of:

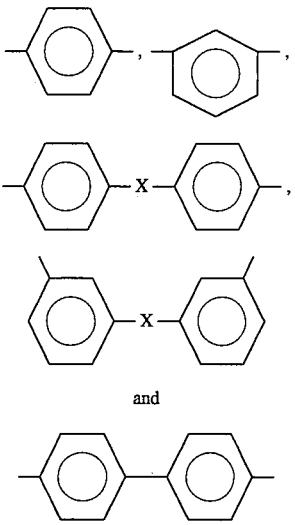

wherein X is as previously defined.

In these thermoplastic hetrocyclic polymers, the number of repeating units is such that the polymer has an intrinsic viscosity of at least 1 dl/g, preferably 2 to 20, inclusive, as determined in methanesulfonic acid at 30° C.

Solvents useful for preparing the composite films include chloroform, chlorobenzene, tetrachloroethane, tetrahydrofuran and the like.

The composite films are prepared by dissolving the 2-ethynyl-5-(4-pyridyl)ethynyl thiophene monomer and the thermoplastic polymer in the common solvent. The quantity of monomer in the film can range from about 5% to about 30%, based on the weight of polymer. For ease of handling, the quantity, by weight, of the monomer/polymer mixture in the solvent can range from about 0.5 to 5.0 percent.

The thin film can be fabricated by spreading the solvent mixture of monomer and polymer onto a suitable surface, by doctor blading, or by spin casting. In general, the film thickness is about 0.2 to 2.0 μm. After forming, the film is dried to evaporate the solvent. The dried film is then poled, e.g., by using a corona discharge produced by imposing +3.5 kV of direct current to a 25 μm thick tungsten wire. While poling, the temperature is raised to about 150°–160° C. and held for 3 hours. The temperature is then raised to about 270° C. for 30 minutes. The film is cooled to room temperature and the field turned off. While heating at 150°–160° C., the terminal acetylenic groups crosslink to provide a polyene structure.

The following examples illustrate the invention:

EXAMPLE 1

2-bromo-5-{2-(4-pyridyl)ethynyl}thiophene 1-(2-thienyl)-2-(4-pyridyl)ethene was prepared by a known procedure.

Bromine (3.77 g; 1.22 ml; 23.54 mmol) was added dropwise to a solution of 1-(2-thienyl)-2-(4-pyridyl)ethene (2.00 g, 10.70 mmol) in 20 ml HBr, kept cold in a salt-ice bath. After complete addition of the bromine, the solution was warmed to room temperature (RT), and then warmed to 35°–50° C. for 2.5–3 hours. The solution was cooled to RT; 200 ml 2N NaOH was added and the mixture stirred for 1 hour, then filtered and the residue dried at 50° C./20 mm Hg for 16 hours. The dried powder was added to 50 ml of t-BuOH containing 2.4 g (21.40 mmol) of t-BuOK. The mixture was heated to reflux for 2.5 hour, then cooled and rotary evaporated to remove most of the t-BuOH. 100 ml of water was added to the reaction concentrate. The resulting mixture was stirred for 1 hour and the precipitate filtered off to obtain a crude product. 1.56 g of purified product (yield: 57.78%) was isolated by chromatography of the material on silica gel using 8:2 THF/hexane as the eluting solvent. TLC (Thin Layer Chromatography) (8:2 THF/hexane): $R_f$=0.47 (starting material $R_f$=0.17), mp=128°–130.5° C. Elemental analysis: Calculated for $C_{11}H_6BrNS$ (mw 264.14): C, 50.02; H, 2.29; Br, 30.25; N, 5.30; S, 12.14. Found: C, 50.01; H, 2.51; Br, 30.84; N, 5.40; S, 11.75.

EXAMPLE II

2-{3-methyl-3-hydroxybutynyl}-5-{2-(4-pyridyl)ethynyl}thiophene

A mixture of 2-bromo-5-{2-(4-pyridyl)ethynyl}thiophene (4.00 g, 15.15 mmol), 2-methyl-3-butyn-2-ol (1.59 g, 18.94 mmol), an adduct of palladium chloride and triphenyl phosphine $PdCl_2(PPh_3)_2$ (0.21 g, 0.30 mmol) and CuI (0.14 g, 0.76 mmol) in degassed triethylamine (50 ml) was strirred at RT for 40 hours, then refluxed for 5 hours. The reaction mixture was cooled and filtered and the filtrate rotary evaporated to obtain a brown oil. The oil was passed through a short column, eluting with 1:1 THF/heptane to obtain a crude product. The crude product was recrystallized from heptane, providing 3.00 g (74.07%) of a light yellow solid. TLC (3:7 THF/hexane): $R_f$=0.21, mp=129.5°–130.1° C. FTIR (KBr) (cm$^{-1}$): 3556–3016 (OH), 2977, 2926 (aliph. C—H), 2201 (C≡C), 1594, 1535, 1445, 1288, 1201, 1167, 998. EIMS: 267 (M$^+$), 252 (M—CH$_3$), 210 (252-CH$_2$CHO).

Elemental analysis: Calculated for $C_{16}H_{13}NOS$ (mw 267.33): C, 71.88; H, 4.90; N, 5.24; S, 11.99. Found: C, 71.11; H, 4.54; N, 4.90; S, 11.35.

EXAMPLE III

2-Ethynyl-5-(4-pyridyl)ethynyl Thiophene

A distillation apparatus was set up and 2-{3-methyl-3-hydroxybutynyl}-5-{2-(4pyridyl)ethynyl}thiophene (8.50 g, 31.84 mmol), KOH (1.78 g, 21.84 mmol) in 25 ml of methanol and 200 ml of toluene were added to the distillation flask. The flask was heated to about 90° C. until all the acetone formed in the reaction and the methanol were collected in the receiving flask (total heating time, about 1.5 to 2 hours). The toluene was removed under reduced pressure and the reddish residue was purified by chromatography on silica gel using 2:8 THF/petroleum ether as the eluting solvent to obtain 4.65 g (69.92% yield) of light yellow solid. TLC (3:7 THF/hexane): $R_f$=0.28, mp=134.5°–135.5° C. FTIR (cm$^{-1}$): 3304 (H—C≡C), 2206 (C≡C). Elemental analysis: Calculated for $C_{13}H_7NS$ (mw 209.26): C, 74.61; H, 3.37; N, 6.70. Found: C, 74.54; H, 3.19; N, 6.72. DSC thermogram of the monomer showed a melting transition at 138° C. and a transition for thermal curing of the terminal C≡C at 144.67° C. TGA thermogram showed about 10–20% weight loss at the terminal C≡C cure temperature (about 150° C.) after which there was little weight loss up to about 400° C.

EXAMPLE IV

Preparation and Curing of Films

Films were cast from 2% solutions in $CHCl_3$ containing 10, 15, 20 and 30% of 2-ethynyl-5-(4-pyridyl)ethynyl thiophene in 6F-PBO-1. Good optical quality films were obtained for the 10, 15 and 20% mixtures. FTIR of the uncured films showed a H—C≡C absorption at 3306 cm$^{-1}$ and an absorption at 2206 cm$^{-1}$ corresponding to the two C≡C stretching vibrations. The films were cured in an oven at 160°, 200° and 250° C. for 20 minutes under a flush of nitrogen. Upon curing the films turned darker but retained their integrity and transparency. For films cured at 160° C., the FTIR showed a less intense H—C≡C absorption at 3304 cm$^{-1}$. This absorption was absent for films cured at 200° and 250° C. All the cured films showed a slightly less intense C≡C absorption at 2206 cm$^{-1}$, corresponding to the uncured internal C≡C. All the cured films could be completely redissolved in chloroform, indicating that relatively little crosslinking occurred during the thermal cure.

EXAMPLE V

Thermomechanical Analysis of Uncured and Cured Films

A thermomechanical analysis (TMA) was performed on the uncured and cured films in order to see the effect of the 2-ethynyl-5-(4-pyridyl)ethynyl thiophene monomer guest on the $T_g$ of the host 6F-PBO-1. A force of 0.01N was found optimum for all films. For the uncured film and for the film cured at 160° C., there was a slight change in dimension at about 125° to 130° C., corresponding to the thermal curing of the monomer. Beyond that, the only change in dimension occurred around the $T_g$ of the host polymer ($T_g$=294° C.). For the films cured at 200° and 250° C., the only change in dimension occurred at about 280° to 285° C. Thus, after curing, the guest monomer, which has been transformed into a thermoset polyene, does not significantly lower the $T_g$ of the host polymer.

EXAMPLE VI

EO Applications

Films of 6F-PBO-1 containing 15% of 2-ethynyl-5-(4-pyridyl)ethynyl thiophene were cured at 225° C. under the influence of an electric poling field. These films exhibited EO coefficients equal to or larger than 10 pm/V, This level of activity could be retained for extended periods at 100° C.

EXAMPLE VII

Insitu Electric Field Poling

Thin films of the monomer (0.03 g) in 6F-PBO-1 (0.15 g) were spin cast from mixtures of chloroform (7.0 g) and chlorobenzene (4.0 g) at 500 rpm on an ITO sputtered glass slide. Film thickness was 0.6 to 0.7 μm. The film was dried at 60°–65° C. for 3 hours. The film was poled using a corona discharge produced by imposing +3.5 kV of direct current to a 25 μm thick tungsten wire. The distance between the film surface and the corona wire was 8 nm. A flow of argon (10 ml/min) was directed onto the film surface during poling. The Second Harmonic Generation (SHG) signal was monitored continuously during the poling sequence. Poling was carried out by first turning on the field and maintaining the sample at room temperature for 45 minutes. The temperature was raised to about 150°–160° C. and held for 3 hours. The temperature was then raised to about 270° C. for 30 minutes. The film was cooled to room temperature and the field turned off. The SHG signal was monitored for the next 12 hours. Upon reaching a stable SHG signal, the sample was removed from the in situ poling stage and the SHG angular dependence measured. The thus-obtained SHG signal value was used to calculate the $\chi^{(2)}$ value by using a Y-cured quartz plate as a standard. Upon cooling the SHG signal decreased rapidly until room temperature was reached. When the field was removed, the signal decayed slowly until a stable value was reached at about 12 hours. This SHG intensity remained constant with a stable $\chi^{(2)}$ value of $2\times10^{-8}$ esu being retained at 100° C. for 22 hours.

Various modifications may be made in the instant invention without departing from the spirit and scope of the appended claims.

We claim:

1. A composite film with second-order nonlinear optical activity consisting essentially of about 5 to 30 weight percent 2-ethynyl-5-(4-pyridyl)ethynyl thiophene, and a high performance thermoplastic polymer having repeating units of the formula:

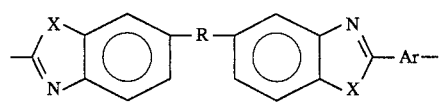

wherein X is —O— or —S—, and R is selected from the group consisting of:

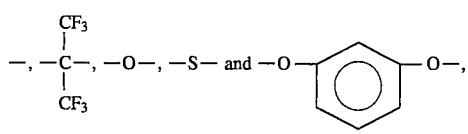

and Ar is selected from the group consisting of:

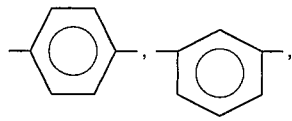

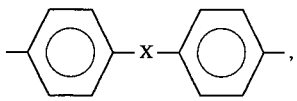

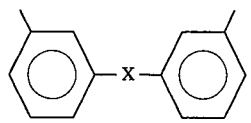

and

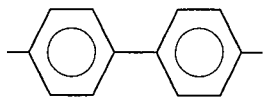

wherein X is as previously defined and said weight percent of 2-ethynyl-5-(4-pyridyl)ethynyl thiophene is based on the weight of the thermoplastic polymer.

2. The composite film of claim 1 wherein R in said thermoplastic polymer is

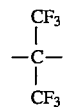

and wherein Ar is

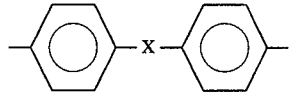

wherein X is —O—.

3. The composite film of claim 2 consisting essentially of about 10 weight percent 2-ethynyl-5-(4-pyridyl)ethynyl thiophene, and said high performance thermoplastic polymer.

4. The composite film of claim 2 consisting essentially of about 15 weight percent 2-ethynyl-5-(4-pyridyl)ethynyl thiophene, and said high performance thermoplastic polymer.

5. The composite film of claim 2 consisting essentially of about 20 weight percent 2-ethynyl-5-(4-pyridyl)ethynyl thiophene, and said high performance thermoplastic polymer.

* * * * *